United States Patent [19]
McGrath et al.

[11] Patent Number: 6,036,631
[45] Date of Patent: Mar. 14, 2000

[54] DEVICE AND METHOD FOR INTRACAVITARY CANCER TREATMENT

[75] Inventors: Jonathan R. McGrath, Chanhassen; Michael R. Forman, Vadnais Heights, both of Minn.

[73] Assignee: Urologix, Inc., Minneapolis, Minn.

[21] Appl. No.: 09/036,942

[22] Filed: Mar. 9, 1998

[51] Int. Cl.⁷ ............................................. A61N 5/00
[52] U.S. Cl. ............................................................ 600/3
[58] Field of Search ............................................. 600/1–8

[56] References Cited

U.S. PATENT DOCUMENTS

| | | | |
|---|---|---|---|
| Re. 34,421 | 10/1993 | Parker et al. | 378/121 |
| 3,750,653 | 8/1973 | Simon | 128/1.2 |
| 3,786,258 | 1/1974 | Schmidt | 250/84.5 |
| 3,866,050 | 2/1975 | Whitfield | 250/497 |
| 4,140,130 | 2/1979 | Storm, III | 128/404 |
| 4,172,979 | 10/1979 | Morrison | 250/505 |
| 4,244,357 | 1/1981 | Morrsion | 128/1.2 |
| 4,510,924 | 4/1985 | Gray | 128/1.2 |
| 4,554,909 | 11/1985 | Torres | 128/1.2 |
| 4,588,395 | 5/1986 | Lemelson | 604/59 |
| 4,631,415 | 12/1986 | Sauerwein et al. | 250/497.1 |
| 4,763,642 | 8/1988 | Horowitz | 128/1.2 |
| 4,763,671 | 8/1988 | Goffinet | 128/786 |
| 4,815,449 | 3/1989 | Horowitz | 600/7 |
| 4,819,618 | 4/1989 | Liprie | 600/7 |
| 4,861,520 | 8/1989 | Van't Hooft et al. | 252/644 |
| 4,872,458 | 10/1989 | Kanehira et al. | 128/401 |
| 4,897,076 | 1/1990 | Puthawala et al. | 600/7 |
| 4,921,327 | 5/1990 | Zito | 350/96.32 |
| 4,927,418 | 5/1990 | Dake et al. | 604/264 |
| 4,947,842 | 8/1990 | Marchosky et al. | 128/401 |
| 4,963,128 | 10/1990 | Daniel et al. | 600/7 |
| 4,968,307 | 11/1990 | Dake et al. | 604/264 |
| 4,969,863 | 11/1990 | Van't Hooft et al. | 600/3 |
| 4,975,240 | 12/1990 | Lahr et al. | 376/260 |
| 4,976,680 | 12/1990 | Hayman et al. | 600/7 |
| 5,007,437 | 4/1991 | Sterzer | 428/786 |
| 5,012,111 | 4/1991 | Ueda | 250/492.3 |
| 5,030,194 | 7/1991 | Van't Hooft | 600/3 |

(List continued on next page.)

FOREIGN PATENT DOCUMENTS

| | | |
|---|---|---|
| 2630012 | 4/1988 | France . |
| 8-215324 | 2/1995 | Japan . |
| WO 93/04727 | 8/1992 | WIPO . |
| WO 97/07740 | 8/1996 | WIPO . |
| WO 97/12540 | 10/1996 | WIPO . |

OTHER PUBLICATIONS

L'irradiation endocavitaire bre've (ce'sium 137) de la loge prostatique dans le cancer localiset' de la postate: re'ultats pre'liminaires apre's 9 ans, P. Jichlinski, P. Douglas et al., Helv.chir. Acta 56, 339–341 (1989).

*Primary Examiner*—Eric F. Winakur
*Attorney, Agent, or Firm*—Kinney & Lange

[57] ABSTRACT

A device and method for treatment of cancerous tissue from a body conduit involves insertion into the body conduit of a probe including an energy-emitting element for delivering ionizing energy. The body conduit is dilated to decrease a distance between at least a portion of the body conduit and the cancerous tissue. Ionizing energy is delivered from the energy-emitting element to selectively injure the cancerous tissue, with dilation of the body conduit minimizing the radiation dose delivered to the body conduit for a given radiation dose delivered to the cancerous tissue.

32 Claims, 9 Drawing Sheets

U.S. PATENT DOCUMENTS

| | | | |
|---|---|---|---|
| 5,044,006 | 8/1991 | Cyrulnik | 378/145 |
| 5,084,001 | 1/1992 | Van't Hooft et al. | 600/3 |
| 5,084,002 | 1/1992 | Liprie | 600/7 |
| 5,090,043 | 2/1992 | Parker et al. | 378/121 |
| 5,092,834 | 3/1992 | Bradshaw et al. | 600/7 |
| 5,095,217 | 3/1992 | Attix | 250/374 |
| 5,103,395 | 4/1992 | Spako et al. | 364/413.26 |
| 5,139,473 | 8/1992 | Bradshaw et al. | 600/3 |
| 5,140,333 | 8/1992 | Parker | 342/371 |
| 5,141,487 | 8/1992 | Liprie | 600/7 |
| 5,153,900 | 10/1992 | Nimikos et al. | 378/65 |
| 5,183,455 | 2/1993 | Hayman et al. | 600/7 |
| 5,199,939 | 4/1993 | Dake et al. | 600/3 |
| 5,267,960 | 12/1993 | Hayman et al. | 604/106 |
| 5,282,781 | 2/1994 | Liprie | 600/3 |
| 5,295,944 | 3/1994 | Teicher | 600/1 |
| 5,322,499 | 6/1994 | Liprie | 600/8 |
| 5,339,347 | 8/1994 | Slatkin et al. | 378/65 |
| 5,364,336 | 11/1994 | Carr | 600/3 |
| 5,369,679 | 11/1994 | Sliski et al. | 378/65 |
| 5,395,300 | 3/1995 | Liprie | 600/3 |
| 5,422,926 | 6/1995 | Smith et al. | 378/121 |
| 5,428,658 | 6/1995 | Oettinger et al. | 378/119 |
| 5,442,678 | 8/1995 | Dinsmore et al. | 378/137 |
| 5,452,720 | 9/1995 | Smith et al. | 128/653.1 |
| 5,496,271 | 3/1996 | Burton et al. | 604/54 |
| 5,498,227 | 3/1996 | Mawad | 600/3 |
| 5,503,614 | 4/1996 | Liprie | 600/7 |
| 5,504,799 | 4/1996 | Suzuki | 378/136 |
| 5,528,652 | 6/1996 | Smith et al. | 378/65 |
| 5,531,662 | 7/1996 | Carr | 600/2 |
| 5,547,454 | 8/1996 | Horn et al. | 600/1 |
| 5,556,389 | 9/1996 | Liprie | 604/264 |
| 5,561,698 | 10/1996 | Mick et al. | 378/162 |
| 5,562,594 | 10/1996 | Weeks | 600/3 |
| 5,566,221 | 10/1996 | Smith et al. | 378/145 |
| 5,575,749 | 11/1996 | Liprie | 600/3 |
| 5,596,619 | 1/1997 | Carol | 378/65 |
| 5,599,796 | 2/1997 | Schinazi et al. | 514/44 |
| 5,602,184 | 2/1997 | Myers et al. | 514/739 |
| 5,611,767 | 3/1997 | Williams | 600/2 |
| 5,618,266 | 4/1997 | Liprie | 604/21 |
| 5,620,479 | 4/1997 | Diederich | 607/97 |
| 5,621,780 | 4/1997 | Smith et al. | 378/65 |
| 5,624,372 | 4/1997 | Liprie | 600/3 |
| 5,626,829 | 5/1997 | Koutrouvelis | 424/1.11 |
| 5,635,709 | 6/1997 | Sliski et al. | 250/252.1 |
| 5,641,755 | 6/1997 | Weichselbaum et al. | 514/44 |
| 5,653,683 | 8/1997 | D'Andrea | 604/21 |
| 5,658,234 | 8/1997 | Dunlavy | 600/9 |
| 5,662,580 | 9/1997 | Bradshaw et al. | 600/3 |
| 5,688,220 | 11/1997 | Verin et al. | 600/1 |
| 5,913,813 | 6/1999 | Williams et al. | 600/3 |

DEVICE AND METHOD FOR INTRACAVITARY CANCER TREATMENT

BACKGROUND OF THE INVENTION

The present invention relates to treatment of cancer, and more particularly to an apparatus and method for delivering ionizing energy to a cancerous volume of tissue from a body conduit while minimizing adverse effects on intervening healthy tissue.

Ionizing radiation treatment of cancer has a therapeutic goal of effectively treating the disease without causing intolerable injury in the process. In the context of treating cancerous body tissues by tissue destruction, such as by delivery of ionizing radiation, a more specific statement of the goal is to destroy a targeted volume of cancerous tissue without destroying healthy tissue. Where ionizing radiation is used, it is important to deliver a sufficient radiation dose to effectively destroy the targeted cancerous tissue while limiting the dose delivered to healthy tissue to a tolerable level.

Ionizing radiation is useful for treating cancer because at certain doses it has a somewhat selective injurious effect on cancerous cells as compared to healthy cells. Cancerous cells have a shorter reproductive life cycle time than normal cells, by definition. Cells are more vulnerable to damage from radiation at certain phases of the reproductive life cycle than others. For a predetermined number of cells, at any given time, more cancerous cells than normal cells are in a vulnerable phase and are therefore vulnerable to radiation damage. Consequently, in the same amount of time, more cancerous cells are injured than healthy cells by the same dose of radiation. Due to the more frequent occurrence of reproductive cell cycle phases, cancerous cells have a shorter opportunity to repair damage and therefore are more statistically likely to be irreversibly damaged by radiation than normal cells. Intermittent or fractionated doses of radiation further improve the ability of radiation therapy to destroy a greater proportion of cancerous tissue.

One technique employed to selectively treat cancerous body tissue is known as external beam radiation therapy (EBRT). According to this method, a target volume of cancerous tissue is located and an external ionizing radiation beam is sequentially focused on the target tissue from multiple angles. The intensity of ionizing radiation from a point source is generally inversely proportional to the square of the distance from the source, so that only a relatively small dose of energy may be delivered from a significant distance to the target tissue by the beam without delivering unacceptably high amounts of energy to intervening tissue between the external beam source and the target tissue. However, this effect is mitigated somewhat by employment of multiple beam angles, with the beam angles being selected to overlap only within the target volume, so that the dose delivered to the target tissue is the sum of the doses delivered by each beam while the dose delivered to intervening tissue is only that provided by a single beam. Another method utilized with EBRT involves delivering fractionated radiation doses. This technique, using multiple sublethal doses, allows intervening healthy tissue to repair the damage induced by radiation in the interval between doses, whereas a greater proportion of cancerous cells undergo reproductive cycle phases. The crossed-beam approach enables EBRT to be used with improved therapeutic effect, although the dose deliverable to the target tissue without harming intervening tissue remains less than optimal.

One significant problem with EBRT is the margin necessary to accommodate movement or shifting of the prostatic capsule. The prostate is not bound in a particular position within the pelvic region of the body, allowing the prostatic capsule to shift upon movement of the body. Mapping of the location of cancerous tissue within the prostate is typically performed in a procedure that is separate from the actual EBRT procedure, such that the cancerous tissue in the prostatic capsule may have shifted from its mapped position during the subsequent EBRT session. In order to ensure that a sufficient dose of radiation is delivered to the cancerous tissue, a margin must be provided to accommodate all of the possible positions of the cancerous tissue; that is, the volume within which the beam angles overlap is increased to include this margin. As a result, healthy tissue located within the margin is necessarily exposed to a higher dose of radiation than would otherwise be desired, limiting the dose deliverable to the cancerous tissue without causing intolerable damage to healthy tissue.

Another approach to treatment of cancerous body tissue involves combining EBRT with radioactive seed implantation, or interstitial brachytherapy. This procedure involves implanting encapsulated radioisotopes in or near the cancerous tissue to be treated, thereby delivering the highest dose of energy to tissue immediately adjacent the radiating seeds, in addition to performing crossed-beam EBRT to deliver radiation energy to the target volume. Seed therapy is often referred to by the broad term brachytherapy, meaning therapy delivered by a source located near or within the diseased area to be treated. The use of radioactive seeds allows the EBRT dose to be reduced. Consequently, the total dose to healthy tissue is reduced, resulting in reduced morbidity (i.e., impotence, incontinence, inflammation). In addition, the problems of displacement of cancerous tissue due to shifting of the prostatic capsule are reduced, since the seeds are able to move along with the targeted cancerous tissue. However, the use of radioactive seeds typically requires an invasive, interstitial implantation procedure that increases the complexity of the procedure and presents a risk of residual morbidity and side effects such as infection, incontinence, or impotence.

There is a continuing need for a minimally invasive solution to deliver effective doses of ionizing radiation to cancerous tissue while controlling doses to healthy tissue at tolerable levels.

SUMMARY OF THE INVENTION

The present invention is a device and method for treatment of cancerous tissue from a body conduit. A probe is inserted into the body conduit, and includes an energy-emitting element for delivering ionizing energy. The body conduit is dilated to decrease a distance between at least a portion of the body conduit and the cancerous tissue. Ionizing energy is delivered from the energy-emitting element to injure the cancerous tissue, with dilation of the body conduit decreasing the radiation dose delivered to the body conduit for a given radiation dose delivered to the cancerous tissue.

In one embodiment, selected energies of ionizing radiation delivered from the energy-emitting element are absorbed, and the selected energies of ionizing radiation absorbed may vary along a length of the energy-emitting element. In another embodiment, at least a portion of the energy-emitting element is shielded to produce a radiation pattern that spatially varies along a length of the probe.

DETAILED DESCRIPTION OF THE PREFERRED EMBODIMENTS

Throughout this detailed description, the present invention will be described as it pertains to transurethral brachytherapy for treatment of prostate cancer. It will be understood by those skilled in the art that certain principles of the present invention may also be applied to treatment of other cancers from nearby body conduits.

Figure 1A:
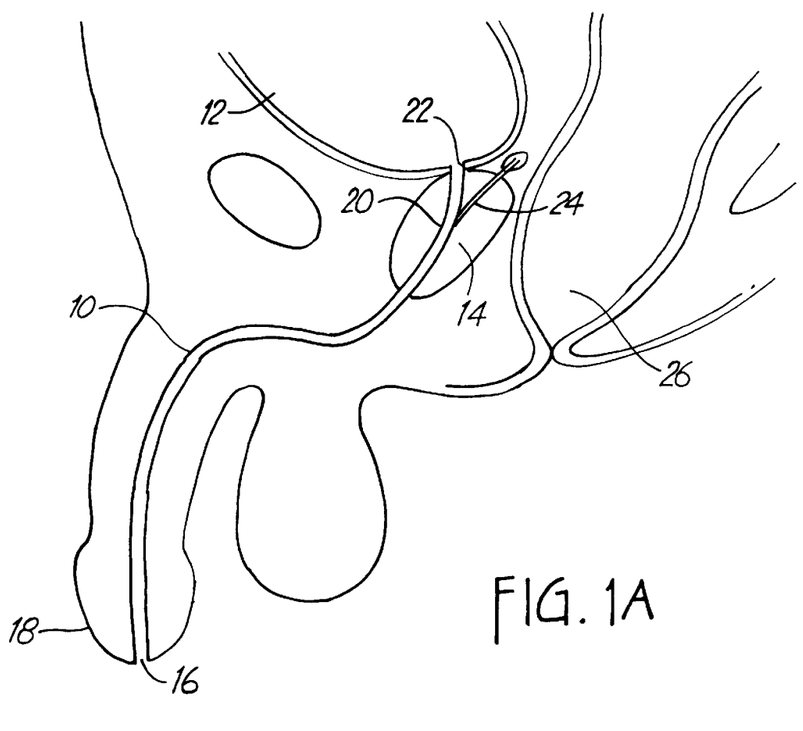
FIG. 1A is a vertical sectional view of a male pelvic region showing the relative position of urinary organs near the prostate.

FIG. 1A is a vertical sectional view of a male pelvic region showing the relative position of urinary organs near the prostate 14. Urethra 10 is a duct leading from bladder 12, through prostate 14 and out orifice 16 of penis end 18. Urethra 10 includes a prostatic portion 20 passing through prostate 14. When prostate 14 is afflicted with cancer, tissue around the periphery of the prostatic capsule is typically among the tissue that is determined to contain cancer. In order to treat the cancerous tissue around the periphery of prostate 14, it is necessary to deliver energy (such as ionizing radiation) to the cancerous tissue with sufficient intensity and for a sufficient time to injure the cancerous tissue. It is also important to avoid intolerable damage to urethra 10 and to adjacent healthy tissues, such as intervening tissue in prostate 14, ejaculatory duct 24 and rectum 26. Selective damage to the cancerous tissue within prostate 14 is made possible by an ionizing energy-delivering probe according to the present invention, which is shown in FIGS. 2A, 2B and 4-7.

Figure 1B:
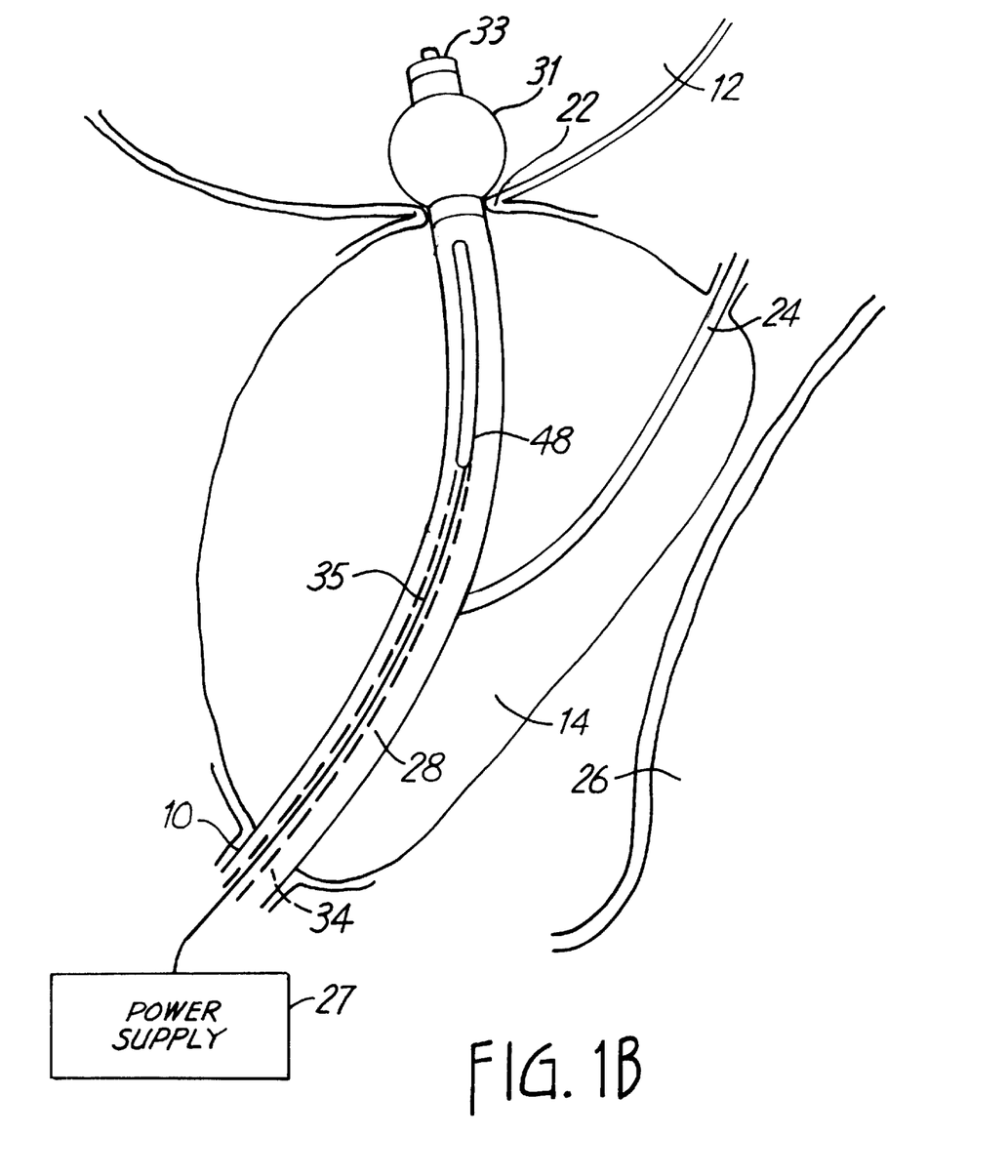
FIG. 1B is an enlarged view of the male pelvic region of FIG. 1A showing a urethral catheter positioned within the prostate region.

FIG. 1B shows an enlarged view of the male pelvic region of FIG. 1A with probe 28 properly positioned within urethra 10. Probe 28 includes a central energy delivery lumen 34 for housing a radiation-emitting source, such as x-ray tube 48 (shown schematically) in one embodiment, with cable 35 provided to couple x-ray tube 48 to power supply 27 in a manner known in the art. In one embodiment, x-ray tube 48 is axially movable along the length of probe 28 to enable treatment of cancerous tissue located anywhere within prostate 14. In another embodiment, a radiation source may be employed that has an active length extending along the entire length of prostate 14, such that axial movement of the radiation source is unnecessary. Cable 35 is preferably a state of the art high voltage coaxial cable exhibiting substantial high voltage holdoff, such as is known in the art for safely delivering high voltage power signals and is commercially available from manufacturers such as New England Wire & Cable, for example. As is known in the art, retention balloon 31 at distal end 33 of probe 28 is inflatable in bladder 12 to secure probe 28 at a predetermined axial location of urethra 10.

Figure 2A:
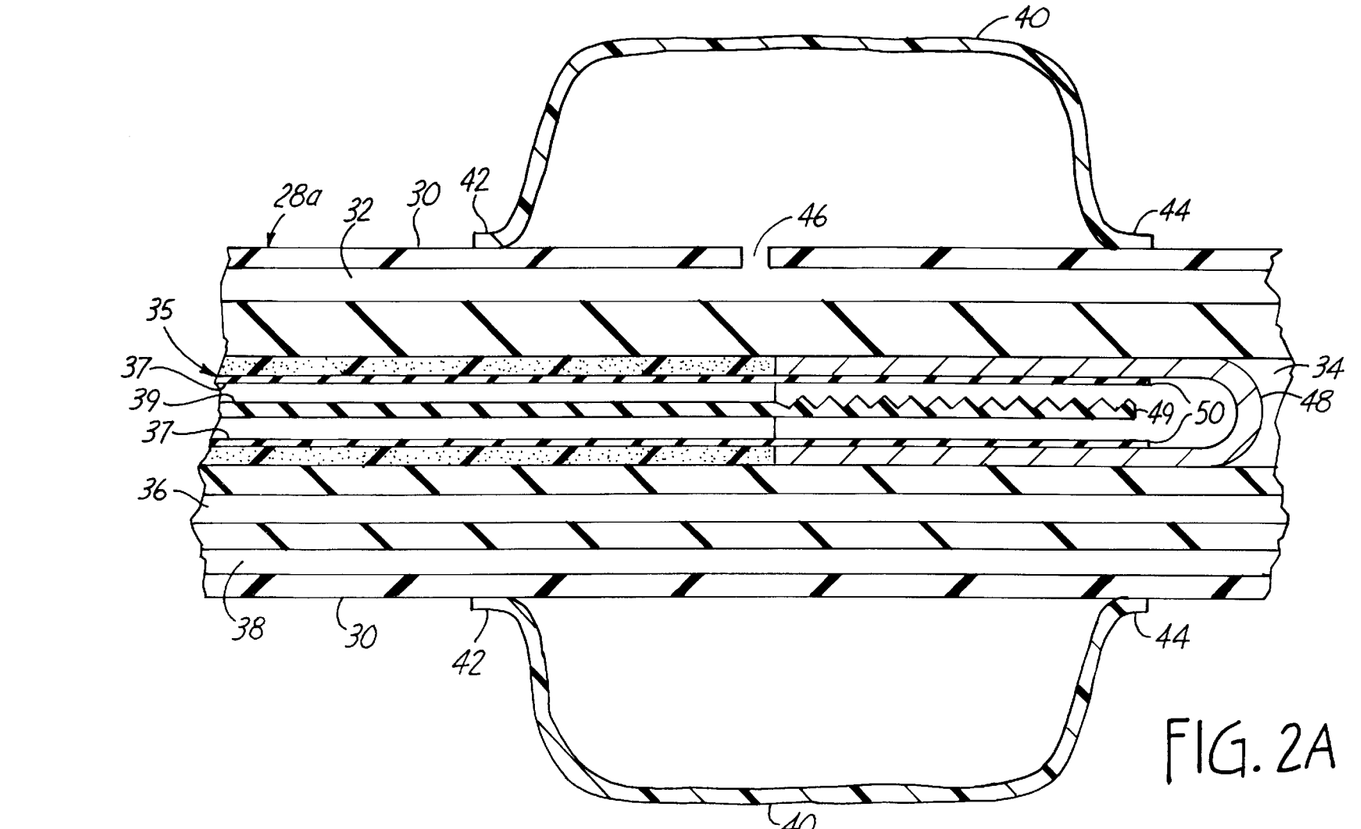
FIG. 2A is a sectional view of an energy-delivering portion of a probe according to a first embodiment of the present invention.

FIG. 2A is a sectional view of an energy-delivering portion of probe 28a according to the present invention, with the radial dimension greatly exaggerated for the sake of clarity. Probe 28a is preferably a Foley-type urethral catheter made of a flexible, medical-grade elastomer, as is known in the art. Probe 28a generally has an outer diameter between about 16 and 22 French, and includes outer surface 30 which is generally circular in cross-section. The overall length of probe 28a allows a distal end thereof to be inserted through urethra 10 and into bladder 12; however, FIG. 2A shows only an energy-delivering portion of probe 28a. In one preferred embodiment, probe 28a is coated with a hydrophilic solution, such as is sold by Hydromer, Inc. under the mark Hydromer, which lubricates outer surface 30 of probe 28a and facilitates its advancement within urethra 10.

Probe 28a is a multi-lumen shaft including dilatation balloon inflation lumen 32, energy delivery lumen 34, urine drainage lumen 36, and retention balloon inflation lumen 38. In some embodiments, probe 28a may further include a cooling system (not shown) for circulation of a cooling fluid to cool the radiation source within energy delivery lumen 34, as well as other lumens for various purposes, as generally described in U.S. Pat. No. 5,300,099 assigned to Urologix, Inc., which is hereby incorporated by reference. Probe 28a also includes dilatation balloon 40 sealingly attached to outer surface 30 and in fluid communication with dilatation balloon inflation lumen 32.

Urine drainage lumen 36 is adapted to facilitate the flow of urine from bladder 12 through probe 28a, in a manner known in the art. Retention balloon inflation lumen 38 is adapted to communicate an inflation fluid to a Foley-type retention balloon 31 (FIG. 1B) at distal end 33 of probe 28a in bladder 12 to locate probe 28a within the urethra, as is known in the art. Urine drainage lumen 36 is generally required only when the duration of treatment is such that the patient will experience discomfort from accumulation of urine within bladder 12 during the treatment session.

Dilatation balloon 40 is secured over probe 28a by bonding balloon waists 42 and 44 over outer surface 30. Dilatation balloon 40 is inflated by supplying pressurized fluid through dilatation balloon inflation lumen 32, which communicates with the interior of dilatation balloon 40 through aperture 46 in outer surface 30 of probe 28a. In an exemplary embodiment, dilatation balloon 40 may be inflated with fluid to a radius extending 0.5 cm beyond outer surface 30 of probe 28a, increasing the typical total distance from the center of probe 28a to the outer surface of dilatation balloon (and thus the wall of urethra 10) from 0.3 cm to 0.8 cm. Balloon 40 may be provided with a larger or smaller radius as necessary for proper treatment. It will be appreciated by one skilled in the art that balloon 40 is a well-known example of a dilatation mechanism, and that other configurations may be used to similarly dilate urethra 10.

In the embodiment shown in FIG. 2A, energy delivery lumen 34 contains a miniature radiation-emitting tube 48 for emitting ionizing radiation radially outwardly from probe 28a. Tube 48 is preferably positioned adjacent dilatation balloon 40, and may for example be movable along the axial length of probe 28a within energy delivery lumen 34.

Radiation-emitting tube 48 is constructed in a manner known in the art, and may for example comprise an evacuated glass tube containing cathode 49 and anode 50. Cathode 49 may for example be connected to inner conductor 39 of coaxial high-voltage cable 35, and anode 50 may for example be connected to outer conductor 37 of cable 35. In an exemplary embodiment, cathode 49 may be a tungsten filament heated to a temperature sufficiently high to cause electrons to reach velocities that allow them to escape from the filament. Anode 50 typically has a very high positive potential, and is positioned around the inside perimeter of tube 48 in an exemplary embodiment, and may also be formed of tungsten. The escaping electrons are attracted to anode 50, and are accelerated to a high velocity before colliding with anode 50 and consequently ejecting inner-shell electrons from the tungsten anode atoms. X-rays and other emissions are created when the high-energy electrons return to normal positions in the tungsten atoms' electron shells. The energy gained by the participating electrons is measured in electron-volts (eV). Tube 48 is preferably operable to produce x-ray radiation photons having energies in the 15 keV to 50 keV range to achieve proper depth penetration (2–3 cm, for example) with the desired dose for treatment of cancerous tissue in prostate 14. It will be understood by one skilled in the art that numerous other cathode and anode configurations and arrangements of high-voltage sourcing cable 35 may be used to achieve the preferred radiation-emitting characteristics of the present invention.

Figure 2B:
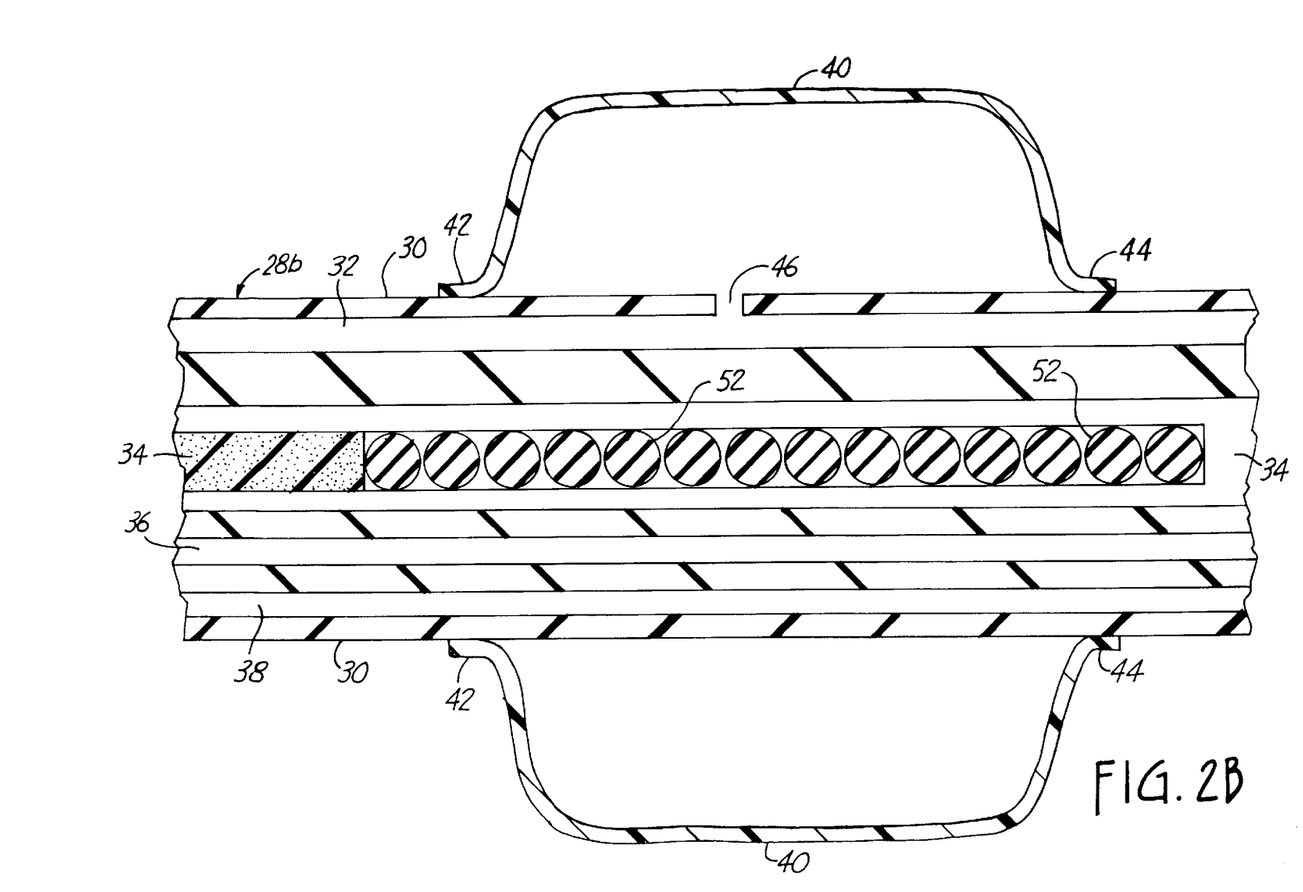
FIG. 2B is a sectional view of an energy-delivering portion of a probe according to a second embodiment of the present invention.

FIG. 2B is a sectional view of an energy-delivering portion of probe 50 according to an alternate embodiment of the present invention. Probe 28b shown in FIG. 2B is identical to probe 28a shown in FIG. 2A, except that energy delivery lumen 34 contains a plurality of radiation-emitting seeds 52 rather than a radiation-emitting tube. FIG. 2B illustrates a plurality of seeds 52 essentially forming a linear source; in an alternative embodiment, a lesser number of seeds may be employed and implemented in such a manner that the seeds are movable along the axial length of probe 28b within energy delivery lumen 34. Seeds 52 are composed of a radiation-emitting material as is known in the art, such as iodine-125, palladium-103 or thallium-201 in exemplary embodiments, typically encased in titanium, for example. Seeds 52 are chosen to operate to produce radiation photons having energies greater than about 15 keV to achieve proper depth penetration (2–3 cm, for example) with the desired dose for treatment of cancerous tissue in prostate 14. In a further alternative embodiment, dilatation balloon 40 may itself be filled with a treatment fluid for emitting ionizing radiation, eliminating the need for energy delivery lumen 34 and a radiation source enclosed therein.

In order to better understand the relationship between radiation intensity and depth of penetration, a brief discussion of the phenomena that occur in tissue upon exposure to x-ray radiation is beneficial. These phenomena are known as Elastic Scattering, Photoelectric Absorption, Compton Scattering, and Electron Pair Production. Elastic Scattering has no substantive effect on x-ray radiation therapy, and Electron Pair Production occurs only at energy levels significantly higher than the 15–50 keV range utilized by the present invention, leaving only Photoelectric Absorption and Compton Scattering of interest.

Photoelectric Absorption is a process where a photon interacts with an electron in one of the inner shells of an atom of the absorbing tissue material, and has a greater probability of occuring when the energy of the photon is equal to the energy binding the innermost electrons in the absorbing tissue material atom. The photon is absorbed by the subject electron, and therefore gives up all of its energy to the subject electron, some of which is used to overcome the binding energy of the electron and release it from its orbit, and the remainder of which is imparted to the electron in the form of kinetic energy of motion. The vacancy left in the atomic shell due to the ejection of the electron must be filled by another electron falling in from an outer shell of the atom or by a conduction electron from outside the atom, causing emission of a low energy photon to balance the decrease in potential energy of the incoming electron.

Compton Scattering is a process where a photon interacts with a "orbital" electron, an electron whose binding energy is negligibly small compared with the energy of the photon. Only a portion of the photon's energy is given to the electron as kinetic energy, and the photon is deflected at an angle and continues on its way with whatever energy remains. The reaction transforms the incident photon into a fast electron and a photon of reduced energy, which may go on to take part in further interactions (either by Photoelectric Absorption or by Compton Scattering, depending on the remaining energy of the photon). In any given case the incident photon may lose very little to a large fraction of its energy. In practice, when an x-ray beam is absorbed by tissue, a vast number of photons interact with a vast number of atoms, and on a statistical basis all possible energy losses will occur. The net result is the production of a large number of fast electrons, many of which can ionize other atoms and initiate the change of events that ultimately is expressed as biological damage.

Therefore, higher energy radiation is able to achieve deeper penetration in tissue than lower energy radiation, due to the higher energy photon's ability to continue on with reduced energy after an interaction. The radiation dose decreases at increasing distances from the radiation source, due to the complete absorption of some of the x-ray photons as the radiation travels through the tissue. For a more complete discussion of the phenomena of radiation absorption, see chapter one of *Radiation for the Radiologist* by Eric J. Hall.

Figure 3:
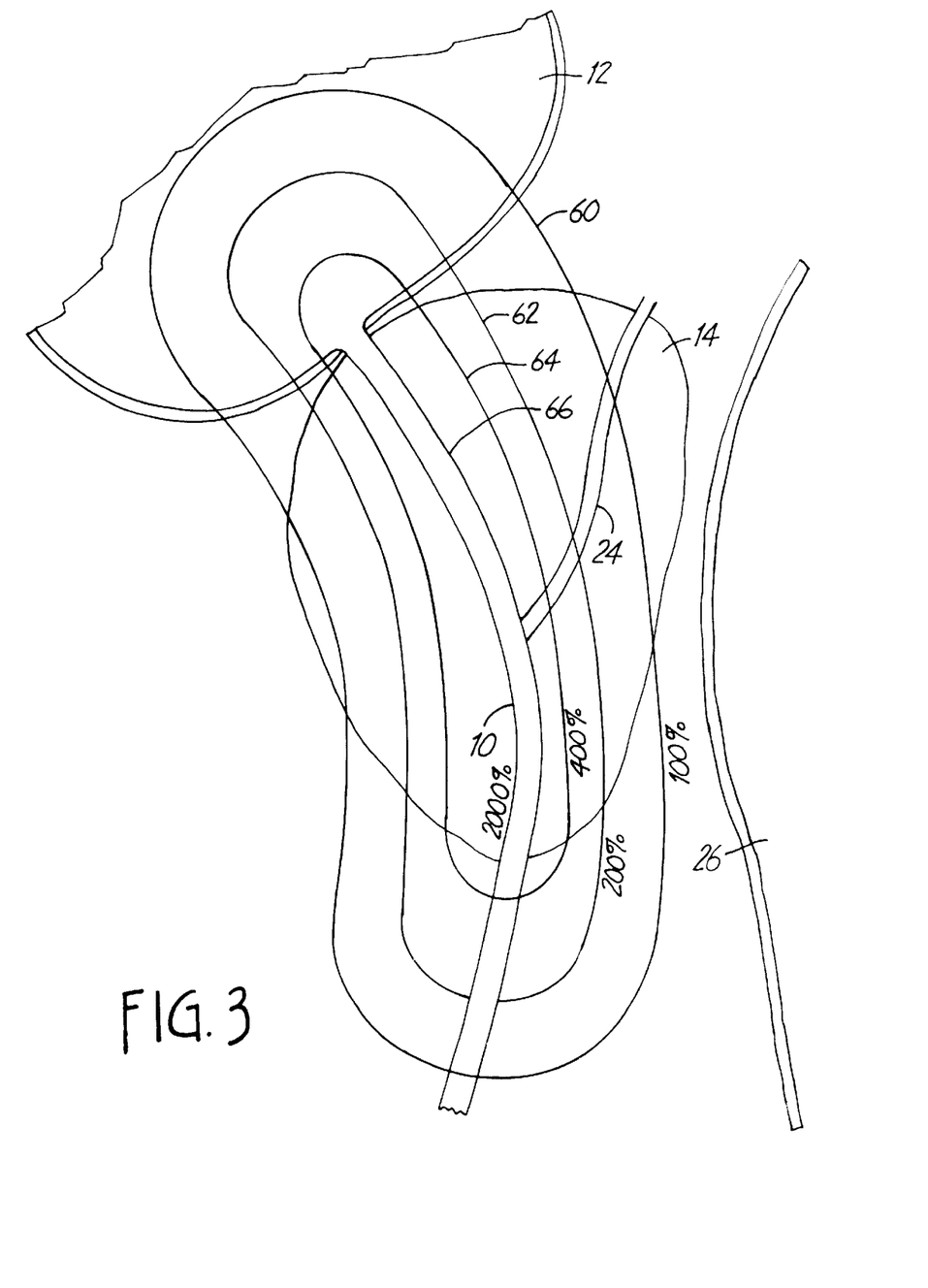
FIG. 3 is a diagram illustrating typical isodose curves for ionizing radiation delivered from the urethra.

FIG. 3 is a diagram illustrating typical isodose curves (that is, curves upon which the dose of ionizing energy delivered to tissue is equal) for ionizing radiation delivered from a source centered within urethra 10 (such as within energy delivery lumen 34 of probes 28a and 28b, FIGS. 2A and 2B). The isodose curves are based on the assumption that a selected target volume of tissue within prostate 14 has been located, and the radiation source within urethra 10 is operated so that the 100% isodose curve 60 runs through the target volume of prostate tissue. Since cancerous prostate tissue is often located near the periphery of prostate 14, FIG. 3 illustrates the 100% isodose curve 60 near the periphery of prostate 14.

For the exemplary case shown in FIG. 3, isodose curve 60 is approximately 2.0 cm from the center of urethra 10. 200% isodose curve 62 is approximately 1.0 cm from the center of urethra 10. 400% isodose curve 64 is approximately 0.5 cm from the center of urethra 10. The wall of urethra 10, when urethra 10 is not dilated, is approximately 0.1 cm from the center of urethra 10 in one exemplary embodiment (where a probe carrying a radiation-emitting source has a radius of 0.1 cm), which is about on the 2000 % isodose curve. The unit Gray (Gy), equal to an energy absorption of 1 joule/kg or 100 rads, is a standard unit of absorbed radiation intensity. Thus, for a desired therapeutic ionizing radiation intensity of 15 Gy (which is within the range suitable as a "boost dose" for use with external beam radiation therapy, for example), the intensity at 200% isodose curve 62 is 30 Gy, the intensity at 400% isodose curve 64 is 60 Gy, and the intensity at the 2000% isodose curve at the wall of urethra 10 is about 300 Gy. For a desired therapeutic ionizing radiation intensity of 100 Gy (which is within a potential range for singular therapy, without requiring any other radiation therapy), the intensity at 200% isodose curve 62 is 200 Gy, the intensity at 400% isodose curve 64 is 400 Gy, and the intensity at the 2000% isodose curve at the wall of urethra 10 is about 2000 Gy.

For the case of the "boost dose" of 15 Gy delivered to the target prostate tissue, the 300 Gy of radiation delivered to the urethral wall could potentially harm the healthy tissue of urethra 10, and could result in some morbidity for the patient. For the case of the therapeutic dose of 100 Gy delivered to the target prostate tissue, the 2000 Gy of radiation delivered to the urethral wall is extremely likely to injure the healthy tissue of urethra 10.

In order to reduce the damage to healthy tissue between the x-ray source and the target prostate tissue, particularly to urethra 10, the present invention operates to dilate urethra 10 while delivering the ionizing energy, thereby decreasing the distance between the urethra and the target prostate tissue. As a result, with 100% isodose curve 60 still defined by the location of the target tissue (2.0 cm from the center of urethra 10), the wall of urethra 10 is essentially displaced outward toward 100% isodose curve 60. An increase in urethral radius from 0.1 cm (the undilated radius) to 0.5 cm (the dilated radius), for example, moves urethra 10 from the 2000% isodose curve to 400% isodose curve 64, reducing the intensity of radiation at urethra 10 by a factor of five. For the "boost dose" example, where the 100% intensity dose is 15 Gy, the radiation intensity at urethra 10 drops from 300 Gy (undilated) to 60 Gy (dilated). For the therapeutic dose example, where the 100% intensity dose is 100 Gy, the radiation intensity at urethra 10 drops from 2000 Gy to 400 Gy. Additional dilatation of urethra 10 decreases the intensity of radiation at urethra 10 even further, potentially to a tolerable dose that will not permanently harm urethra 10, particularly in combination with fractionation of the dose delivered. The present invention therefore provides a solution for delivering ionizing radiation to cancerous prostate tissue from a minimally invasive urethral probe while decreasing the damage to intervening healthy tissue such as the wall of urethra 10.

Prostate 14 (see, e.g., FIG. 1A) is not entirely stationary within the pelvic region of the body. Movement of the body, or even dilatation of urethra 10, could potentially cause displacement of the prostatic capsule. The present invention is still effective when dilatation of urethra 10 causes prostate 14 to be displaced further away from urethra 10, because of the geometric properties of the displacement and of radiation therapy.

Geometrically, an increase in the radius of urethra 10 increases the radius of prostate 14 as well, but by a lesser amount. For the sake of clarity, urethra 10 may be modeled as a cylinder of radius $R_1$ and prostate 14 may be modeled as a sphere of radius $R_2$. Consider an example of a probe that has a radius of 0.3 cm and contains a radiation-emitting source, such that urethral radius $R_1$ is 0.3 cm, and a prostate having a prostatic radius $R_2$ of 2.25 cm. The prostatic portion of the urethral cylinder therefore has a length (l) of 4.5 cm (equal to the diameter of the prostatic sphere). The volume ($V_1$) of the urethral cylinder is expressed as:

$$V_1 = \pi R_1^2 l$$

and the volume of the prostatic sphere ($V_2$) is expressed as:

$$V_2 = \frac{4}{3}\pi R_2^3$$

Thus, $V_1$ is 1.27 cm³ for the model parameters given above. When $R_1$ is increased by dilatation of urethra 10 from 0.3 cm to 0.8 cm, for example, $V_1$ increases to 9.04 cm³. Thus, the volume of prostate tissue that is displaced by dilatation of urethra 10 is the difference between the two urethral volumes, or 7.77 cm³. This displaced volume of tissue essentially appears as an expansion of the outer perimeter of the prostatic sphere. The volume of the prostatic sphere when urethra 10 is not dilated is 47.7 cm³ for the model parameters given above. By adding the volume of tissue displaced by dilatation of urethra 10 (7.77 cm³) to the volume of the prostatic sphere when urethra 10 is not dilated (47.7 cm³), the total volume of the prostatic sphere when urethra 10 is dilated is determined as 55.47 cm³. Inserting this number into the equation for the volume of the prostatic sphere given above and solving for the radius yields a value of 2.36 cm for $R_2$. Thus, an increase in the radius of urethra 10 from 0.3 cm to 0.8 cm (0.5 cm increase) results in an increase in radius of prostate 14 from 2.25 cm to 2.36 cm (0.11 cm increase). The increase in the radius of prostate 14 is therefore significantly less than the increase in the radius of urethra 10 due to dilatation. Thus, only a small increase in the radiation energy delivered from a probe within urethra 10 is required to reach the perimeter of prostate 14 at the target dose level. Even though the radiation energy delivered from the probe is slightly increased, the increased spatial separation between the radiation-emitting source within urethra 10 and the dilated wall of urethra 10 results in a significant net decrease in the radiation intensity delivered to the wall of urethra 10.

The geometric effect explained above is further enhanced by the nature of radiation dosimetry, where an increase in radius has a greater dose reduction effect close to the source than distant from the source. The radiation-emitting source is modeled as a linear source (which may be implemented by an actual linear source such as a row of seeds or a ribbon, or by a point source swept along the axial length of tissue to be treated), in which case the intensity of radiation delivered to tissue is generally proportional to the inverse of the radial distance from the source. In the example given above, the urethra is dilated from 0.3 cm to 0.8 cm in radius, and the peripheral prostate tissue is displaced from a radius of 2.25 cm to 2.36 cm. In order to provide an effective radiation dose to the periphery of prostate 14, the energy of the radiation-emitting source must be increased to shift the 100% isodose curve outward from 2.25 cm to 2.36 cm. For a therapeutic dose example, where the radiation dose at the 100% isodose curve is 100 Gy, Table 1 shown below summarizes the doses delivered at various distances from the center of urethra 10 for both the undilated case (urethral wall at 0.3 cm, prostatic capsule at 2.25 cm) and the dilated case (urethral wall at 0.8 cm, prostatic capsule at 2.36 cm):

TABLE 1

|  | 0.3 cm | 0.8 cm | 1.0 cm | 2.0 cm | 2.25 cm | 2.36 cm |
|---|---|---|---|---|---|---|
| Undilated | 750 Gy (750%) | 281.3 Gy (281.3%) | 225 Gy (225%) | 112.5 Gy (112.5%) | 100 Gy (100%) | 95.3 Gy (95.3%) |
| Dilated | 786.7 Gy (786.7%) | 295 Gy (295%) | 236 Gy (236%) | 118 Gy (118%) | 104.9 Gy (104.9%) | 100 Gy (100%) |

As shown in Table 1, dilatation of the urethra from 0.3 cm to 0.8 cm reduces the radiation dose delivered to the urethra from 750 Gy to 295 Gy (over a factor of 2.5), a significantly more tolerable level of radiation. Greater or lesser dilatation of urethra 10 may be effected according to the radiation dose delivered to urethra 10 required to prevent intolerable damage to urethra 10 and the characteristics of morbidity associated therewith for a given radiation dose delivered to cancerous tissue.

In an alternative embodiment of the invention, prostate 14 may be prevented from moving by employing certain methods to stabilize the prostatic capsule. For example, bladder 12 may be filled with fluid to prevent the prostatic capsule from being dilated toward bladder 12. A spatula or other hard instrument may be inserted in rectum 26 to prevent the prostatic capsule from being displaced toward rectum 26. These procedures effectively obviate the need to increase the intensity of the radiation source within urethra 10 for outward displacement of target tissue in prostate 14, thereby also reducing the radiation dose delivered to urethra 10 at any particular radius. Dilatation according to the present invention further reduces the radiation dose delivered to urethra 10 by increasing the distance from the radiation source to the urethra for the predetermined target tissue location.

Figure 4:
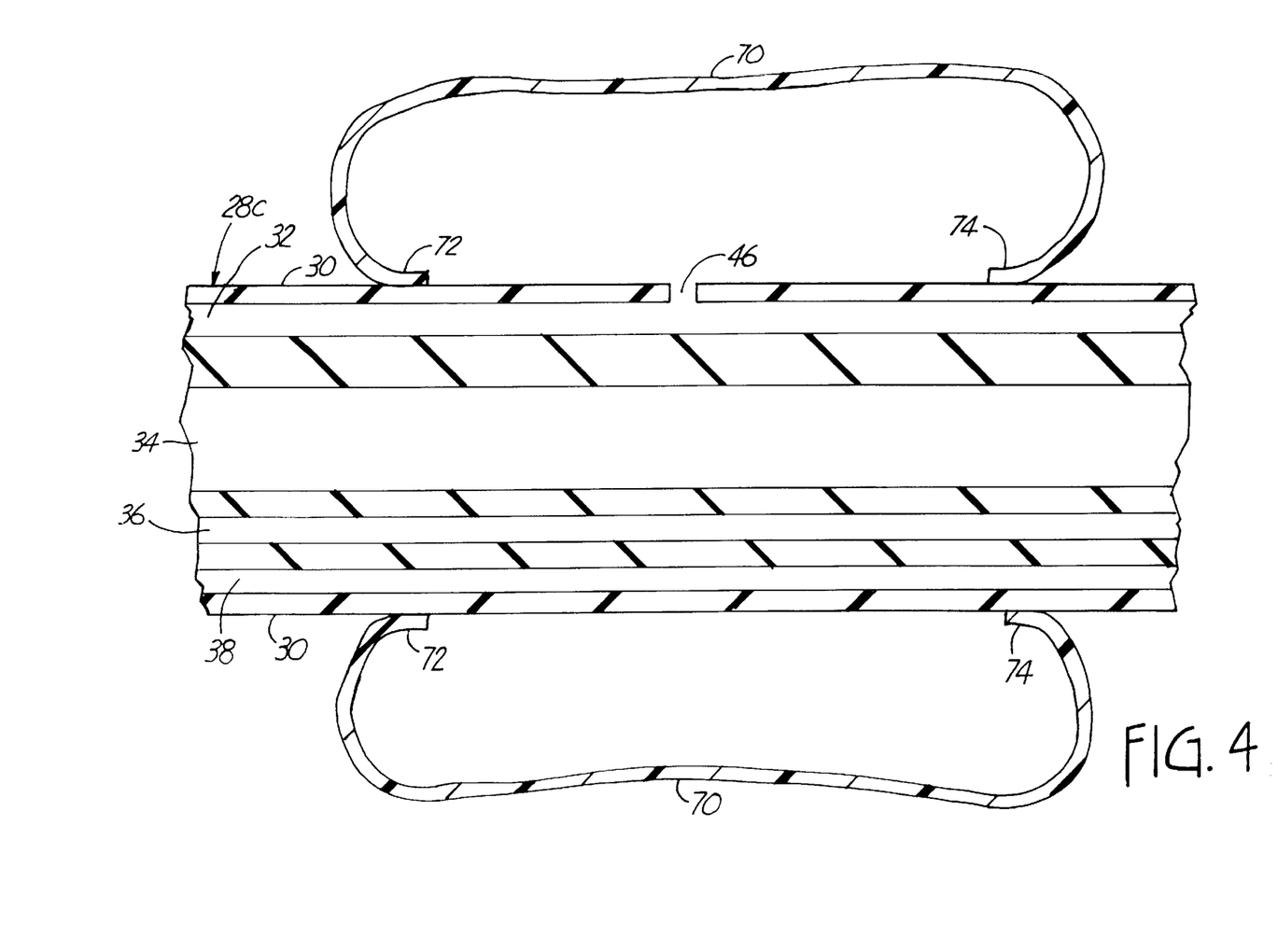
FIG. 4 is a sectional view of an energy delivering portion of a probe according to a third embodiment of the present invention.

Probe 28a for implementing the present invention, shown in FIG. 2A, illustrates a conventionally shaped dilatation balloon 40, which is inflatable to dilate urethra 10 during delivery of ionizing radiation and thereby minimize damage to urethral tissue. FIG. 4 shows an energy-delivering portion of an alternate probe 28c (with the radiation source within energy delivery lumen 34 omitted for the sake of clarity) utilizing an inflatable dilatation balloon 70 having a shape when inflated that approximates the shape of the 400% isodose curve (see FIG. 3). By approximating the shape of the isodose curve, balloon 70 is able to ensure that all points of urethra 10 receive the same dose of ionizing radiation, so that the entire urethra 10 is affected in the same way by the radiation therapy treatment.

In order to further minimize the damage done to urethra 10 during radiation therapy, dilatation balloon 40 (FIGS. 2A and 2B) or dilatation balloon 70 (FIG. 4) may be inflated with a fluid containing metallic particles. The metals for commixing with the fluid used to inflate the dilatation balloon are selected to absorb radiation having energies at the low end of the therapeutic radiation range, thereby reducing the effects of the radiation near the energy source (which ordinarily is substantially affected by the low energy radiation) while having a lesser impact on the effects of the radiation distant from the energy source (which ordinarily is affected very little by the low energy radiation). The atomic number of the metal particles substantially determines the efficiency of radiation that they absorb, and the choice of metals to achieve the goal of absorbing certain radiation energies is within the expertise of one skilled in the art. The overall effect of introducing the metal particles into the dilatation balloon inflation fluid is to reduce the radiation dose delivered to the wall of urethra 10.

Figure 5:
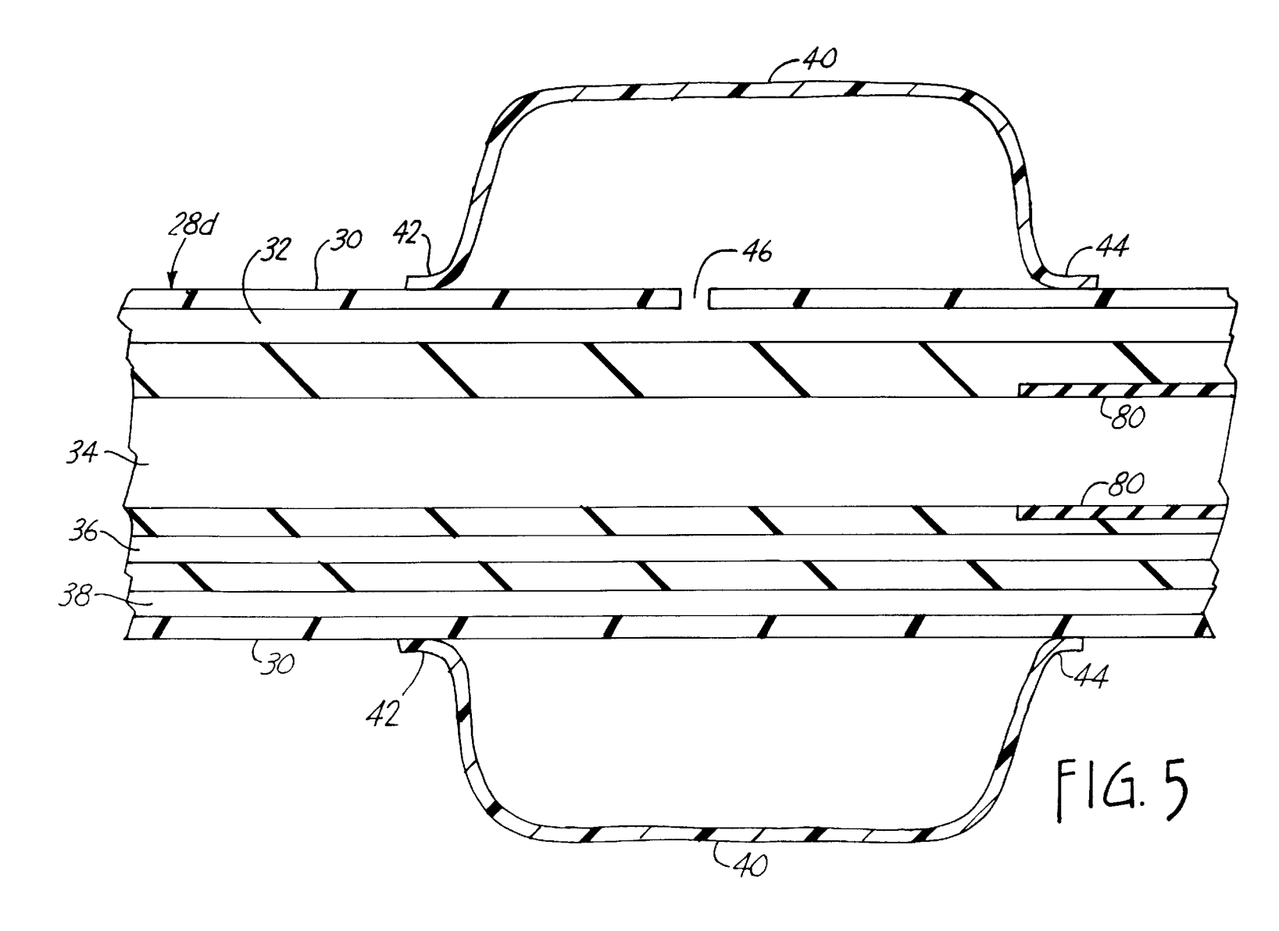
FIG. 5 is a sectional view of an energy-delivering portion of a probe according to a fourth embodiment of the present invention.

As shown in FIG. 3, delivering ionizing radiation to target tissue in prostate 14 from an unshielded radiation source in urethra 10 exposes tissue around the neck of bladder 12 (at the junction of urethra 10 and bladder 12) to radiation, which could potentially lead to undesirable side effects such as incontinence. FIG. 5 is a sectional view of a probe 28d (with the radiation source within energy delivery lumen 34 omitted for the sake of clarity) that is similar to probes 28a (FIG. 2A), 28b (FIG. 2B) and 28c (FIG. 4) except for the addition of tubular metal shield 80 around energy delivery lumen 34. Metal shield 80 is composed of a material that absorbs ionizing radiation of particular energy levels, so that a radiation dose profile may be controlled and shaped to protect tissue adjacent the bladder neck and lower sphincter, for example, to avoid potential undesirable side effects resulting from exposure of those regions to radiation. In the embodiment shown in FIG. 5, shielding 80 is provided around the portion of energy delivery lumen 34 that is located adjacent the bladder neck when probe 28d is inserted into urethra 10, thereby reducing the radiation dose delivered in the bladder neck region. In other embodiments, multiple shields such as metal shields 80 may be provided along the length of a source within energy delivery lumen 34, composed of different metals and/or different thicknesses of metals along the length of the source to produce more complex radiation dose profiles, as desired for a particular treatment goal. A tubular outer sleeve, for example, may be provided over outer surface 30 of probe 28d (with appropriate cut-out sections to accommodate the dilatation balloon) to provide the shielding effect. The sleeve may be composed of different metals or and/or thicknesses of metals along its length, or multiple outer sleeves may be provided, fitting over one another, to vary the shielding effect along the length of probe 28d. The sleeve or sleeves may be in a fixed position, or may be movable along the length of probe 28d. A sleeve, or multiple sleeves, may alternatively be provided directly over a tube containing the x-ray source within energy delivery lumen 34, to achieve a similar shielding effect.

Figure 6:
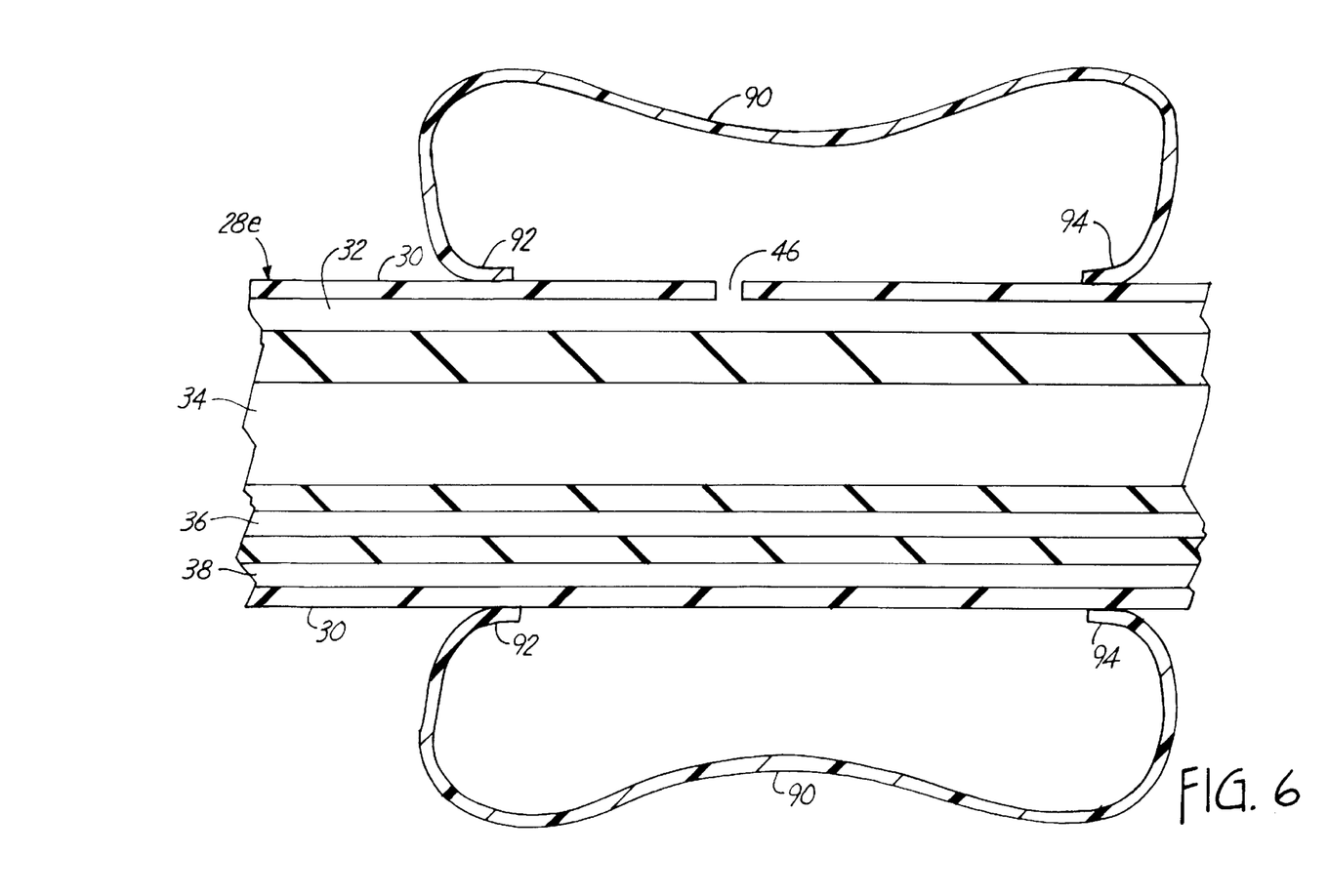
FIG. 6 is a sectional view of an energy-delivering portion of a probe according to a fifth embodiment of the present invention.

FIG. 6 is a sectional view of probe 28e (with the radiation source within energy delivery lumen 34 omitted for the sake of clarity) having shaped dilatation balloon 90 for selectively shielding areas of tissue during radiation treatment. Dilatation balloon 90 is attached to outer surface 30 of probe 28e at waists 92 and 94, and is inflated by pressurized fluid flowing through dilatation balloon inflation lumen 32. The inflation fluid is imbued with metal particles to absorb particular energies of ionizing radiation. The "barbell" shape of dilatation balloon 90 presents a thicker cross-section of fluid at the ends of balloon 90, thereby providing greater shielding in those regions. Thus, a greater intensity of radiation is delivered through the central portion of dilatation balloon 90, and a lesser intensity of radiation is delivered to the bladder neck region adjacent the end of balloon 90, reducing the possibility of undesirable side effects due to radiation exposure of tissue adjacent bladder 12. Other shapes of balloon 90 may be used to vary the radiation dose pattern along the axial length of probe 28e and protect vulnerable anatomical areas from ionizing radiation.

Figure 7:
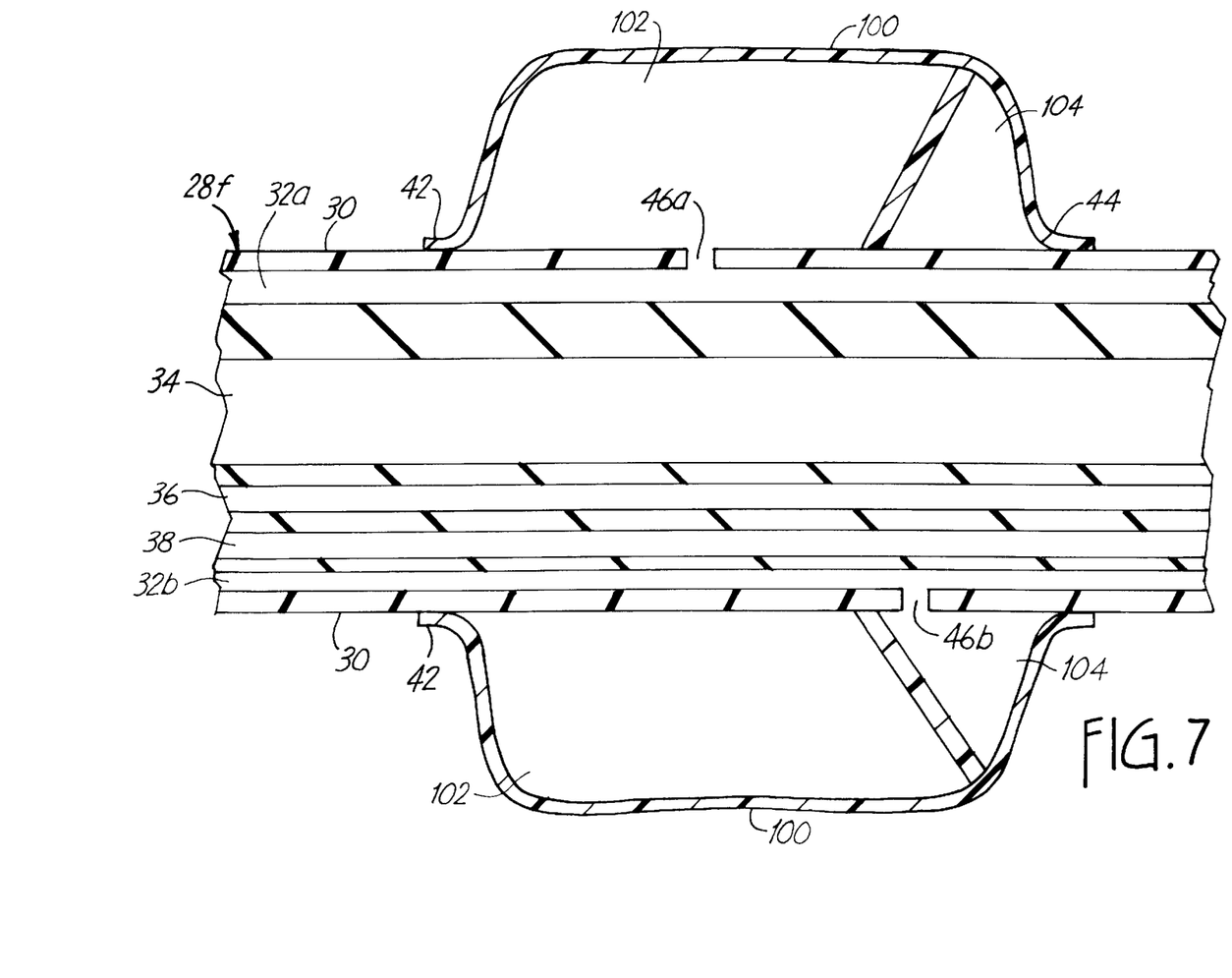
FIG. 7 is a sectional view of an energy-delivering portion of a probe according to a sixth embodiment of the present invention.

FIG. 7 is a sectional view of probe 28f (with the radiation source within energy delivery lumen 34 omitted for the sake of clarity) utilizing dilatation balloon 100 having compartments 102 and 104 therein. Compartment 102 is inflated with pressurized fluid flowing through dilatation balloon inflation lumen 32a into compartment 102 through aperture 46a. The fluid for inflating compartment 102 is imbued with metal particles to absorb ionizing energy at a first energy level. Compartment 104 is inflated with pressurized fluid flowing through dilatation balloon inflation lumen 32b into compartment 104 through aperture 46b. The fluid for inflating compartment 104 is imbued with metal particles to absorb ionizing energy at a second energy level, higher than the first energy level, to provide greater protection from ionizing radiation for tissue adjacent compartment 104. A plurality of compartments may be provided in balloon 100 with inflation fluids having different metal particles commixed in each compartment, to produce more complex radiation dose patterns. Alternatively, a plurality of separate balloons may be provided along the length of probe 28f, each inflated with fluids having different metal particles commixed therein, to produce the desired radiation dose patterns.

In all embodiments of the present invention described above where prostate tissue near the bladder neck does not receive a therapeutic radiation dose due to selective spatial filtering, the tissue may be treated separately by a number of methods. For example, external radiation may be used to target the untreated tissue, radioactive seeds may be placed within the untreated tissue interstitially, or a miniature radiation source may be placed adjacent the lower sphincter. Other methods will be apparent to one skilled in the art. In some cases, it may not even be necessary to separately treat the tissue near the bladder neck, if that tissue is not a part of the targeted cancerous volume of tissue (that is, if the tissue near the bladder neck is not cancerous).

The present invention therefore provides an apparatus and method for treating cancerous tissue from a nearby bodily conduit while minimizing damage to intervening healthy tissue. Various radiation dose patterns may be achieved, to deliver selected amounts of ionizing radiation to different tissue regions. With a radiation-emitting source preferably located at a fixed radius in the bodily conduit, the conduit is dilated to decrease the distance between at least a portion of the bodily conduit and the cancerous tissue, thereby decreasing the radiation dose delivered to the bodily conduit for a given dose delivered to the cancerous tissue.

Although the present invention has been described with reference to preferred embodiments, workers skilled in the art will recognize that changes may be made in form and detail without departing from the spirit and scope of the invention.

We claim:

1. A device for treatment of cancerous prostate tissue from a urethra, comprising:
   a probe adapted to be inserted into the urethra, including a retention balloon inflatable in a bladder and an energy-emitting element for delivering ionizing energy to the cancerous prostate tissue; and
   a dilator at least partially surrounding the energy-emitting element.

2. The device of claim 1, wherein the probe includes a balloon inflation lumen and the dilator comprises an inflatable dilatation balloon secured to an outer surface of the probe, the balloon being in fluid communication with the inflation lumen.

3. The device of claim 2, wherein the dilatation balloon is inflatable to a radius of about 0.5 cm from the outer surface of the probe.

4. The device of claim 2, wherein the energy-emitting element is capable of delivering ionizing radiation having a first intensity at a first radial distance from the probe corresponding to a periphery of the prostate, and having a second intensity of about four times the first intensity at a second radial distance from the probe corresponding to a periphery of the dilatation balloon when inflated.

5. The device of claim 4, wherein the first intensity is about 15 Gy and the second intensity is about 60 Gy.

6. The device of claim 2, wherein the dilatation balloon is inflated with a filtering fluid for absorbing selected energies of the ionizing energy delivered by the energy-emitting element.

7. The device of claim 6, wherein the filtering fluid is imbued with metal particles selected to absorb the selected energies of ionizing radiation.

8. The device of claim 6, wherein the dilatation balloon has a shape when inflated with a first thickness at an end of the dilatation balloon and a second thickness less than the first thickness at a center of the dilatation balloon.

9. The device of claim 6, wherein the dilatation balloon includes a plurality of compartments along a length of the probe.

10. The device of claim 9, wherein each of the plurality of compartments is inflated with a different filtering fluid to absorb different energies of ionizing radiation along the length of the probe.

11. The device of claim 1, wherein the energy-emitting element comprises a radiation tube.

12. The device of claim 1, wherein the energy-emitting element comprises at least one radiating seed.

13. The device of claim 1, wherein the energy-emitting element is movable along an axial length of the probe.

14. The device of claim 1, further comprising shielding means around the energy-emitting element for producing a radiation pattern that spatially varies along a length of the probe.

15. The device of claim 14, wherein the shielding means comprises at least one tubular metal shield around at least a portion of the energy-emitting element.

16. The device of claim 15, wherein the at least one tubular metal shield is located around an outer surface of the probe.

17. The device of claim 15, wherein the at least one tubular metal shield is composed of a plurality of metals along its length.

18. The device of claim 14, wherein the probe includes at least one balloon inflation lumen and the shielding means comprises at least one inflatable dilatation balloon secured to an outer surface of the probe, the at least one dilatation balloon being in fluid communication with the at least one inflation lumen and being inflatable with a filtering fluid for absorbing selected energies of the ionizing energy delivered by the energy-emitting element.

19. The device of claim 18, wherein the filtering fluid is imbued with metal particles selected to absorb the selected energies of ionizing radiation.

20. The device of claim 18, wherein the at least one inflatable dilatation balloon comprises a compartmentalized balloon having a plurality of compartments and the at least one inflation lumen comprises a plurality of inflation lumens, respective ones of the inflation lumens being in fluid communication with respective compartments of the compartmentalized balloon.

21. The device of claim 20, wherein each of the plurality of compartments receives a different filtering fluid to absorb differing energies of ionizing radiation along the length of the probe.

22. The device of claim 18, wherein the at least one inflatable dilatation balloon comprises a plurality of dilatation balloons and the at least one inflation lumen comprises a plurality of inflation lumens, respective ones of the inflation lumens being in fluid communication with respective ones of the plurality of dilatation balloons.

23. The device of claim 22, wherein each of the plurality of dilatation balloons receives a different filtering fluid to absorb differing energies of ionizing radiation along the length of the probe.

24. A method of treating cancerous prostate tissue comprising:
   inserting a probe including an energy-emitting element into a urethra, the probe further including an end portion which extends into a bladder;
   securing the end portion of the probe at a base of the bladder;
   dilating the urethra; and
   delivering a predetermined intensity of ionizing energy from the energy-emitting element for a time sufficient to destroy the cancerous prostate tissue.

25. The method of claim 24, wherein the step of dilating the urethra comprises increasing a radius of the urethra to about 0.5 cm.

26. The method of claim 24, wherein the step of dilating the urethra comprises inflating a balloon secured to an outer surface of the probe.

27. The method of claim 26, wherein the balloon is inflated to a radius of about 0.5 cm from the outer surface of the probe.

28. The method of claim 26, wherein ionizing energy is delivered from the energy-emitting element with a first intensity at a first radial distance from the probe corresponding to a periphery of the prostate, and with a second intensity of about four times the first intensity at a second radial distance from the probe corresponding to a periphery of the balloon when inflated.

29. The method of claim 24, further comprising absorbing selected energies of ionizing radiation delivered from the energy-emitting element.

30. The method of claim 29, wherein the selected energies of ionizing radiation absorbed vary along a length of the energy-emitting element.

31. The method of claim 24, further comprising shielding at least a portion of the energy-emitting element to produce a radiation pattern that spatially varies along a length of the probe.

32. The method of claim 24, wherein the step of securing the end portion of the probe at the base of the bladder comprises inflating a retention balloon at the end portion of the probe.

* * * * *